United States Patent [19]
Yoshizato et al.

[11] Patent Number: 5,350,583
[45] Date of Patent: * Sep. 27, 1994

[54] CELL-PENETRABLE MEDICAL MATERIAL AND ARTIFICIAL SKIN

[75] Inventors: Katsutoshi Yoshizato, Ebina; Jun Konishi, Fuji; Mikio Koide, Fuji; Kaori Oyamada, Fuji; Ken-ichi Ohsaki, Fuji; Takeo Katakura, Fuji; Yuichi Mori, Tokyo; Ken Tatebe, Fuji, all of Japan

[73] Assignee: Terumo Kabushiki Kaisha, Tokyo, Japan

[*] Notice: The portion of the term of this patent subsequent to Nov. 23, 2010 has been disclaimed.

[21] Appl. No.: 970,955

[22] Filed: Nov. 3, 1992

Related U.S. Application Data

[63] Continuation of Ser. No. 576,494, Sep. 7, 1990, abandoned.

[30] Foreign Application Priority Data

Mar. 9, 1988 [JP] Japan .................................. 63-53836
Jul. 25, 1988 [JP] Japan ................................ 63-183478
Sep. 6, 1988 [JP] Japan ................................ 63-221337

[51] Int. Cl.$^5$ .............................................. A61F 2/10
[52] U.S. Cl. ............................. 424/484; 128/DIG. 8; 424/423; 424/424; 623/1; 623/15; 623/66; 623/901
[58] Field of Search ........................ 424/484, 423, 424; 128/DIG. 8, 156; 623/1, 15, 66, 901; 530/356; 525/937

[56] References Cited

U.S. PATENT DOCUMENTS

| | | | |
|---|---|---|---|
| 4,060,081 | 11/1977 | Yannas et al. | 128/156 |
| 4,233,360 | 11/1980 | Luck et al. | 128/DIG. 8 X |
| 4,294,241 | 10/1981 | Miyata | 128/156 |
| 4,522,753 | 6/1985 | Yannas et al. | 530/356 |
| 4,597,762 | 7/1986 | Walter et al. | 623/15 X |
| 4,642,118 | 2/1987 | Kuroyanagi et al. | 623/15 |
| 4,689,399 | 8/1987 | Chu | 128/156 X |
| 4,703,108 | 10/1987 | Silver et al. | 424/94.64 X |
| 4,883,487 | 11/1989 | Yoshizato et al. | 623/15 |
| 4,931,546 | 6/1990 | Tardy et al. | 530/356 |
| 5,015,584 | 5/1991 | Brysk | 623/15 X |
| 5,141,747 | 8/1992 | Scholz | 424/424 |
| 5,147,514 | 9/1992 | Mechanic | 204/157.68 |
| 5,263,983 | 11/1993 | Yoshizato et al. | 623/12 |

OTHER PUBLICATIONS

Woodroof, E. Aubrey Ph.D., "Biobrane®, A Biosynthetic Prothesis".

Primary Examiner—Thurman K. Page
Assistant Examiner—Robert H. Harrison
Attorney, Agent, or Firm—Burns, Doane, Swecker & Mathis

[57] ABSTRACT

Cell-penetrable medical material made of denatured collagen which is prepared by heating, in the presence of water is disclosed, the collagen having cross-linking structure. Artificial skin prepared by using this medical material as a wound-contacting layer (2) is also disclosed.

19 Claims, 1 Drawing Sheet

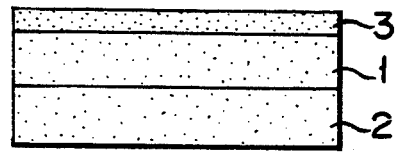
F I G. 1A
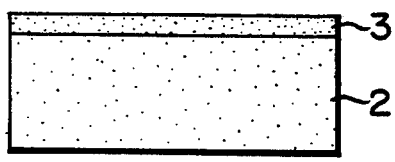
F I G. 1B
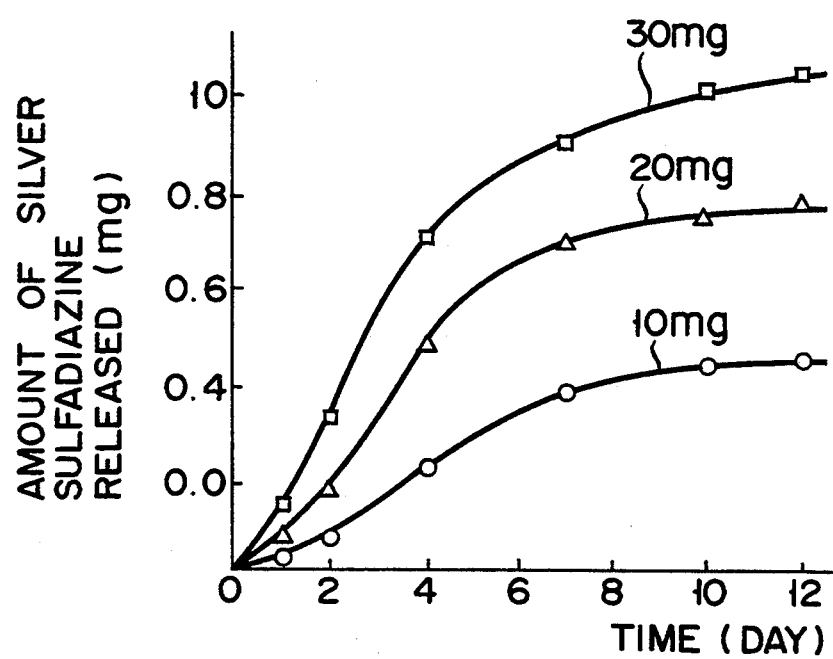
F I G. 2

CELL-PENETRABLE MEDICAL MATERIAL AND ARTIFICIAL SKIN

This application is a continuation of application Ser. No. 07/576,494, filed Sep. 7, 1990, abandoned.

TECHNICAL FIELD

The present invention relates to cell-penetrable medical material easily assimilable into living tissues and useful as artificial tissues. Further, the present invention also relates to application of this medical material to artificial skin.

BACKGROUND ART

Implantation is very effective for treating deficiency occurred in part of tissues or irreversible function deficiency. For avoiding the problem of immune incompatibility known as rejection, in this case, it is preferable to transplant the tissue coming from other regions of the patient or his relatives, namely allotransplantation. However, such favorable implanting tissues are not always available. So, such studies for providing implantable artificial tissues have heretofore been made.

First approach for getting artificial tissues free of rejection is to provide the material having low histological reactivity, namely the material which fails to sensitize the tissue and immunocellular system. An example of this approach is the study to enhence hydrophobicity of the synthetic polymer material represented by polyurethanes.

Second approach is to provide the material which is capable of assimilating rapidly into the tissue before inducing the immunoreaction thereby functioning as a part of an organ. More particularly, it is to construct the tissue similar to connective tissues by penetrating such a cell having the tissue-healing function as fibroblast into the material coming from living bodies such as collagen. Since the new tissue thus formed is no longer not-self, no immune incompatibility would take place. Therefore, it can be said that this approach is more ideal than the first approach.

However, said second approach has the following defects.

Artificial materials consisting of collagen or the like derived from living bodies show high affinity to cellular tissues, but would be easily decomposed by collagenase or other enzymes within the living bodies. Therefore, there cannot be sufficiently kept the time for the penetration of fibroblast or the like to construct new tissues. So it is necessary to enforce the physical properties of the material by introducing cross-linking with any means, in order that the material may resist against the decomposition due to collagenase. Dehydrating cross-linking under heating or chemical cross-linking with chemicals can be adopted therefore. Of these cross-linking methods, the dehydrating cross-linking is safer than the chemical treatment, but less resistant against collagenase than the chemical cross-linking. Therefore, it is general that the chemical cross-linking is adopted singly, otherwise a combination of the chemical cross-linking and the dehydrating cross-linking is adopted.

Resistance against collagenase is markedly improved by introducing the cross-linking structure by said methods. For example, when the cross-linking structure is introduced into a collagen by merely dehydrating the collagen under heating at 110° C. in vacuum for 24 hours, the cross-linked collagen is dissolved within one day by allowing to stand at 37° C. in 3 unit/ml collagenase solution. On the contrary, the collagen obtained by introducing the cross-linking structure with an isocyanate type cross-linking agent does not show any change on appearance in 7 days even by allowing to stand still at 37° C. in 1000 unit/ml collagenase solution.

On the other hand, introduction of said strong cross-linking structure would lower markedly the good affinity to cells or tissues, which is an inherent property of the collagen. Therefore, the penetration of cells would be inhibited to accompany a problem that the new desired tissues could not be formed.

As stated above, it is difficult to suffice both the requirement of good resistance to enzymes and the requirement of good affinity to cells or tissues in materials derived from living bodies such as collagen. Therefore, while the second approach is very attractive, no medical material sufficing the requirements has been developed yet.

The cell-penetrable medical material may be considered to be very useful as coating material for imbedding artificial organs or artificial vessels. However, its use as artificial skin is more realizable and effective.

Artificial skin is an artificial medical material used for coating temporarily or eternally the injured region in order to prevent bacterial infections or overflowing of the humor when any dermal tissue is injured by burning or ambustion. Thus, artificial skin is a replacement for autograft skin.

As a wound coating material which can be used for the same purpose as in artificial skin, gauze, absorbent cotton and the like are heretofor used. However, these materials have a disadvantage that they have low inhibitory ability against bacterial infections. In addition, because they absorb rapidly the exudate, the surface of wound would be dried so much and accompanied by pain, bleeding or the like in peeling them. Although sometimes an ointment or the like is used together for avoiding said problem, in this case there would take place another disadvantage that the exudate is so insufficiently absorbed that the surface of wound become excessively moist.

When the surface of a wound extends in a broad scope, the following coating films are used. First category includes silicone gauze, silicone rubber film, synthetic fiber sheet such as nylon, teflon or the like having velour-like superficial structure, and other synthetic materials. Second category includes lyophilizated pig's skin, chitin unwoven cloth, collagen film, polyamino acid sponge, mucopolysaccharide complex collagen film, and other materials derived from living bodies.

However, coating films made from said synthetic materials have disadvantages such as poor tight adhesion to the injured region and low steam permeability together with easy inclination to induce cracking. Further, said coating films derived from living bodies show comparatively better adaptability to living bodies but have difficulty in availability of raw material. Moreover, most of them have antigenicity as well as defects such as inclination to deteriorate by bacterial infection or contact with the exudate.

In addition to said coating films, certain complex film made from collagen-treated nylon mesh and silicone film has recently been developed and is commercially available. This complex film has favorable close adhesion to the surface of wound and appropriate water permeability. However, the complex film adheres to the surface of wound, because the granulation tissue enters into the nylon mesh in the course of curing. Since the nylon mesh remains in the granulation tissue without decomposition, after curing the complex film must be peeled together with remarkable pain.

DISCLOSURE OF THE INVENTION

A first object of the present invention is to provide cell-penetrable medical material which, because of having the desired resistance to decomposing enzymes, can keep the necessary mechanical strength over a certain period under in vivo circumstances together with favorable affinity to cells and tissues, and also to provide a process for preparing said material.

A second object of the present invention is to provide artificial skin which has a satisfactory function as a replacement of autograft skin, using said medical material, and also to provide a process for preparing it. Thus, artificial skin of the present invention scan inhibit bacterial infection and overflowing of the body fluid by coating temporarily or eternally the surface of wound and can accelerate sufficiently repairing the tissue due to cell growth.

The cell-penetrable medical material of the present invention is characterized in consisting essentially of denatured collagen which is obtained by heating, in the presence of water, collagen having the cross-linking structure.

The process for preparing the cell-penetrable medical material comprises a step of subjecting collagen to cross-linking treatment to give the collagen having cross-linking structure and a step of heating, at 50° to 125° C. in the presence of water, the collagen having cross-linking structure.

A first artificial skin of the present invention comprises a supporting layer made of fibroin, a wound contacting layer laminated on one side of said supporting layer and a water permeation-controlling layer for controlling water permeation laminated on the other side of said supporting layer, said wound-contacting layer consisting of denatured collagen obtained by heating, in the presence of water, the collagen having cross-linking structure. Further, it is preferable to incorporate antibacterial agent into at least one layer of the wound-contacting layer, the supporting layer and the water permeation-controlling layer.

A second artificial skin of the present invention comprises a wound-contacting layer and a water permeation-controlling layer for controlling water permeation laminated on one side of said wound-contacting layer, said wound-contacting layer consisting of denatured collagen obtained by heating, in the presence of water, the collagen having cross-linking structure. Further, it is preferable to incorporate antibacterial agent into at least one of the wound-contacting layer and the water permeation-controlling layer.

The present invention will be explained in detail as follows:

CELL-PENETRABLE MEDICAL MATERIAL AND A PROCESS FOR PREPARING IT

Cell-penetrable medical material of the present invention is based on the discovery of the fact that cell can easily penetrate into the denatured collagen prepared by heating, in the presence of water, the collagen having cross-linking structure and that the necessary mechanical properties can be kept over a prescribed period under in vivo circumstances.

The collagen having cross-linking structure can be prepared by introducing cross-linking structure in a conventional manner.

As starting collagen to which cross-linking is introduced, there is exemplified the collagen consisting of triple chain helix which is obtained by treating collagen derived from bovine dermis with an acid or alkali. Preferably it is desirous to use the collagen lack of antigenic part (telopeptide) at the terminal of collagen molecule. Such collagen lacking of antigenicity and free of this telopeptide is known by the trademark "Atelocollagen," in general. ATELOCOLLAGEN can be prepared by treating the starting collagen with an acid or alkali, as stated above, and then with pepsin specifically working on telopeptide. More preferably, these starting collagens are used as fibrous collagen. Such fibrous collagens can be prepared by neutralizing the collagen consisting of triple chain helix with phosphate buffer at 37° C. Thereby the water soluble and dispersed triple chain helix structure is reconstructed into a fibrous structure having periodicity, whereby the collagen is insolubilized.

For introducing cross-linking structure into the collagen, there are adopted a method of dehydrating the collagen and a method of treating the collagen with a cross-linking agent. The dehydrating is performed by heating the collagen at 50° to 180° C. under vacuum of not exceeding 0.05 Torr. for 1 to 24 hours, preferably 100° to 120° C. under said vacuum for 2 to 8 hours. When treated with a cross-linked agent, the cross-linking agent used is not particularly limited. For example, there are exemplified aldehyde type cross-linking agents such as glutaraldehyde, isocyanate type cross-linking agent such as hexamethylene diisocyanate and carbodiimide type cross-linking agent such as 1-ethyl-3 (3-dimethylaminopropyl)-carbodiimide hydrochloride.

Introduction of such cross-linking structure improves mechanical strength of the collagen and raises resistance against enzymatic decomposition. This effect is more remarkable in fibrous collagen than in dispersed type triple chain collagen. Thus, introduction of such cross-linking structure into fibrous collagen leads to marvelous improvement of physical properties such as mechanical strength by synergistic action between fibrous structure and cross-linking structure. When the degree of cross-linking to be introduced into the collagen is too low, no sufficient physical strength can be obtained. When it is too high on the contrary, the structure and favorable properties of collagen are damaged. Therefore, it is necessary to set appropriately the cross-linking degree depending upon various conditions. For example, when any cross-linking agent is used for fibrous collagen, appropriate cross-linking degree can be obtained by using in general 0.01 to 5% (w/v), preferably 1 to 3% (w/v) of cross-linking agent.

Subsequently, the collagen containing said cross-linking structure thus obtained is denatured under heating. Heating is made in the presence of water at 50° to 125° C., preferably 90° to 121° C. over a period of 20 minutes to 1 hour. Since the helix structure of the raw collagen is modified by this heating into random coil, the helix content rate becomes an index of denaturation degree. More accurately, the denaturation degree is represented by [1-(Helix content rate)]. Appropriate helix content rate of denatured collagen used in the present invention is 0 to 80%, preferably 40 to 70%.

Further, said helix content rate can be measured with circular dichroism spectrometer (CD) or infra red spectrophotometer [p. L. Gorden et at., Macromoles, 1 (6), 954, 1974; Masanobu Nakura, Hashimoto, et al., Polymer Article Collection, 41 (8), 473, 1984]. Values of the helix content rate used in the present application were calculated on the basis of data of this spectrometer. Moreover, it has been found from the result of electrophoresis that a part of the collagen molecule is cleaved in said denatured collagen.

As described above, it seems that cells can penetrate easily into the denatured collagen, because the helix is converted into random coil and a part thereof is cleaved on the way in the denatured collagen molecule used in the present invention. On the contrary, it is apt to undergo decomposition with collagenase through the denaturation and is decomposed comparatively rapidly. However, as described above, cross-linking structure is introduced prior to said denaturation, and resistance to enzymatic decomposition with collagenase or the like is afforded. By contribution of this cross-linking structure, there can be kept the time for penetration of fibroblast or the like and for construction of new tissues. Thus, the part having the cross-linking structure forms a skelton structure resistant to decomposing action of enzymes, in the collagen after the thermal denaturation.

As stated above, the medical material of the present invention can attain excellent cell-penetration, and on the other hand sufficient strength can be kept until dermis-like connective tissues can be formed by penetration of cells. Further, since the whole is finally decomposed and absorbed by undergoing enzymatic action, it can be completely assimilated in vivo.

The medical material of the present invention can be made in an appropriate form either before or after introducing the cross-linking structure into the collagen. In any case, thermal denaturation in the presence of water can be made under the appropriate form.

The following methods can be adopted for making the appropriate form. If the solution of collagen before cross-linking treatment is used, there is used a method of forming films by solvent-casting or a method of forming porous sponge by lyophilization. When aqueous collagen solution after cross-linking treatment is used, a method can be adopted, in which the collagen solution is gelled and the gel thus obtained is then shaped.

Artificial Skin

Artificial skin of the present invention is a multi-layer complex film comprising said cell-penetrable medical material.

First Artificial Skin

This artificial skin is typically a three-layered complex film as shown in FIG. 1A. In FIG. 1, 1 is a supporting layer made from fibroin film. Below said supporting layer 1 a wound-contacting layer 2 is laminated, and over the supporting layer 1 a water permeation controlling layer 3 is laminated. Said cell-penetrable medical material is used in wound-contacting layer 2. These layers are hereafter explained in detail, respectively.

(1) Wound-contacting Layer 2

For wound-contacting layer 2 is used said cell-penetrable medical material. Thus, wound-contacting layer 2 is made of denatured collagen obtained by heat-treating the collagen having cross-linking structure. Composition and the like of this wound-contacting layer are not explained in detail, because they are described above. Necessarily, this wound-contacting layer can take various forms such as film, sponge or the like, as described above on those of medical materials.

Wound-contacting layer 2 has a function that it softly protects the surface of the wound by covering directly the wound, lowers pain, affords appropriate water and inhibits bacterial infection. Further, it accelerates new formation of the tissues with cell growth and stimulates curing. Said wound-contacting layer 2 made of cell-penetrable materials has all these functions and in particular exceeds markedly in accelerating new formation of the tissues. Thus, once it is applied on the surface of the wound, inflammatory cells such as macrophage, neutrophile or the like are infiltrated together with rapid invasion of fibroblast. As a result, dermis-like connective tissues are constructed to accelerate curing of the wound. Since this invasion of cells are described in detail on the medical material above, its explanation is abridged. Further, this wound-contacting layer 2 is finally decomposed by enzymes to be absorbed into the living body. Accordingly, it is not necessary to accompany marked pain for removing the artificial skin, as seen in known artificial skins.

(2) Supporting Layer 1

Supporting layer 1 enforces mechanical strength of wound-contacting layer 2 and makes the penetration of cells into wound-contacting layer 2 smooth.

As stated above, the wound-contacting layer has prescribed resistance against collagenase by using fibrous collagen together. However, since the mechanical strength as coating materials are still insufficient and finally the wound-contacting layer is assimilated into the living body, any supporting body for protecting it from the outside stimulations is necessary. So, supporting layer 1 is needed to have mechanical strength exceeding certain level. At the same time, supporting layer 1 should not inhibit invasion of cells into wound-contacting layer 2. Fibroin is used as material for sufficing these requirements.

Fibroin is material derived from living bodies and is a protein which is a main constituent of silk. As appreciated from the fact that silk is used for suture for surgical operation, fibroin is a protein excellent in stability in living bodies. Aqueous solution of fibroin can be prepared by dissolving fibroin in a concentrated neutral solution of salts such as lithium bromide or calcium chloride and subjecting the solution to dialysis or the like. This aqueous solution of fibroin is freezed at −18° C. to 0° C. and defrosted to form β-type crystalline structure, thereby giving water insoluble porous unwoven cloth [Jun Umagoshi, Kobunshi Kagaku (Polymer Chemistry), 30, 582 (1973)]. This porous unwoven cloth of fibroin shows more excellent stability in living bodies than ordinary collagen having cross-linking structure. So, it is appropriately used as a supporting layer of artificial skin used for coating the surface of wound over a long period of time.

(3) Water Permeation Controlling Layer 3

Water permeation controlling layer 3 functions to control water content on the surface of wound during artificial skin is applied on the surface of wound. Pooling exudate on the surface of wound can be avoided while keeping the surface of wound wet and moist, by ensuring appropriate steam permeation with this water permeation controlling layer 3. At the same time, transudation of the protein ingredients in the exudate outside can be prevented, thereby making favorable circumstances for repairing tissues. It is heretofore well known that such water permeation controlling layer is used in wound coating material, and these known materials can be also used for artificial skin of the present invention. Thus, a film of non-toxic material having about 0.1 to 1 mg/cm$^2$/hour of water flux can be used as such water permeation controlling layer 3. Its appropriate thickness is about 5 to 200 μm. Non-toxic materials include silicone resin, polyacrylate ester, polymethacrylate ester, polyurethane and the like. In particular, silicone resin is preferred.

Said artificial skin having three layers can exhibit very excellent therapeutic effect as artificial skin, because wound-contacting layer 2 has favorable cell-penetration and appropriate resistance against enzymic decomposition, satisfactory mechanical strength is given by supporting layer 1 and appropriate water content is kept on the surface of wound by water permeation controlling layer 3. Since an improvement of cell-penetration and resistance to enzymes, both of which were heretofore incompatible, have been attained in wound-contacting layer 2, there can be obtained by far more excellent therapy accelerating effect than known wound coating materials.

In preferred embodiments of said artificial skin, antibacterial agent is incorporated in at least one of such wound-contacting layer 2, supporting layer 1 and water permeation controlling layer 3. Appropriate antibacterial agents include silver sulfadiazine, gentamycin and silver nitrate. However, various other antibacterial agents can be used without limiting to them. Incorporation of such antibacterial agents is a means for preventing effectively bacterial infection.

Bacterial infection is apt to occur in broad ambustion or serious ambustion (for example, degree III ambustion). Cream base containing antibacterial agent has heretofore been used for preventing such bacterial infection. However, when cream base is used together with known wound coating material such as gauze or bandage, about 57% of the applied cream soaks into gauze or the like together with the exudate and about 21% of the cream only gets to the surface of wound. Further, the cream has to be applied everyday to need troublesome labor. On the contrary, if the artificial skin of the present invention contains antibacterial agent, it can release gradually the antibacterial agent in a certain period. Therefore, the antibacterial agent can act continuously without exposing the surface of wound to ambient air and without troublesome labor in applying the antibacterial agent to the wound everyday, whereby bacterial infection can be prevented effectively in combination with bacterial penetration-preventive effect of the water permeation controlling layer.

The following experiment was performed for examining the aspect of releasing antibacterial agent contained in water permeation controlling layer 3. At first, three silicone films (about 0.15 g) of 20 μm thick in size (5 cm×5 cm) were prepared, which respectively contain 10 mg, 20 mg and 30 mg of silver sulfadiazine (AgSD). These respective samples were dipped in 100 ml of distilled water, and the amount of AgSD eluted was measured in the lapse of time, respectively. The result is shown in FIG. 2. In this Figure, the abscissa shows the lapse of time (day) and the ordinate shows the cumulative amount of AgSD eluted. It is observed from the result that AgSD contained in the silicone film is gradually released to attain the gradual releasability enough to get the effect described above.

When a main object is to prevent bacterial invasion from outside and it is necessary to add antibacterial agent into any one of these layers, it is preferred to select water permeation controlling layer 3. On the other hand, when the surface of wound is already infected by bacteria and a lot of antibacterial agent is needed to be applied on the wound, it is desirable to incorporate antibacterial agent into either wound-contacting layer 2 or supporting layer 1. Of course, one can incorporate antibacterial agent into any two or three members of wound-contacting layer 2, supporting layer 1 and water permeation controlling layer 3.

Second Artificial Skin

This artificial skin is a complex film consisting of wound-contacting layer 2 and water permeation controlling layer 3 as typically shown in FIG. 1B. Thus, the second artificial skin is lack of supporting layer 1, but otherwise quite same as described in first artificial skin.

Production of Artificial Skin

Said first artificial skin can be prepared easily, for example, according to the following steps a) to h).

a) At first aqueous solution of collagen (preferably fibrous collagen) is prepared.

b) Alternatively, porous fibroin film to use as supporting layer 2 is prepared according to the method already described.

c) Subsequently, said collagen solution is contained in a certain vessel, and said fibroin film is set on the liquid surface and lyophilized. Thereby a laminate consisting of supporting layer 1 made of fibroin film and porous collagen layer 2' is obtained.

d) Cross-linking structure is introduced into porous collagen layer 2' obtained in Step C). The method for the cross-linking procedure may be either dehydration by heating or treatment with cross-linking agent.

e) A solution to afford water-permeable film such as silicone or the like is developed on a teflon substrate or the like having peeling surface, thereby giving viscous thin film.

f) Said laminate subjected to cross-linking treatment in Step d) is set on the viscous thin film of Step e). In this case supporting layer 2 is set so as to contact with the viscous thin layer.

g) Said viscous thin film is dried up to hardening and heated at 50° to 180° C. under vacuum not exceeding 0.05 Torr for 1 to 24 hours. Thereby said viscous thin film is dried and water permeation controlling layer 3 is formed. At the same time said controlling layer 3 is bound with said supporting layer 1 as a whole.

h) three layers-laminate obtained in Step g) is heated at 90° to 121° C., preferably 90° to 121° C. for 20 minutes to 1 hour in the presence of water. Thereby the collagen containing cross-linking structure which constitutes porous layer 2' is denatured and converted into the desirous wound-contacting layer 2. Thus artificial skin consisting of three layers structure (FIG. 1A) is obtained.

Further, cross-linking treatment may be effected under solution in Step a) in place of the cross-linking treatment in Step d).

Moreover, the porous collagen film (preferably fibrous collagen having cross-linking structure) may be used in place of fibroin film as supporting layer 1 above. The porous film of fibrous collagen having cross-linking structure is prepared by lyophilizing aqueous solution of fibrous cross-linking collagen obtained above. However, since the cross-linking collagen film used in supporting layer 1 is also denatured by Step g) in this case, supporting layer 1 is not distinctive from wound-contacting layer 2. So, artificial skin obtained in this case is not three layers-structure (FIG. 1 A) but two layers-structure (FIG. 1B).

Artificial skin in two layers (FIG. 1B) can be easily prepared also by the following Steps a) to d).

a) At first aqueous solution of collagen (preferably fibrous collagen) is prepared. Then, cross-linking agent is added to said aqueous solution to give aqueous solution of collagen having cross-linking structure.

b) Aqueous solution of cross-linked collagen thus obtained is gelled and formed into the shape of wound-contacting layer 2 in FIG. 2.

c) Solution of such a substance to afford water permeable film as silicone or the like is developed on a polytetrafluoroethylene substrate or the like having peeling surface to give viscous thin film.

d) Cross-linked collagen in the shaped form obtained in Step b) is set on this viscous thin film.

e) Said viscous thin film is dried up to hardening and heated at 50° to 180° C. under vacuum not exceeding 0.05 Torr, for 1 to 24 hours. Thereby said viscous thin film is dried to give water permeation-controlling layer 3 and at the same time said water permeation-controlling layer 3 is bound to said supporting layer 1 as a whole.

f) Said two layers-laminate obtained in Step e) is heated at 90° to 121° C., preferably 90° to 121° C. for 20 minutes to 1 hour in the presence of water. Thereby the collagen having cross-linking structure which constitutes porous layer 2' is denatured and converted into the desired wound-contacting layer 2. Thus, there is obtained artificial skin having two layers structure in FIG. 1B.

Further, denaturation of the cross-linked collagen may be performed under the shaped form obtained in Step b) in place of the denaturation in Step f).

Furthermore, even in any preparing processes above, favorable artificial skin containing said antibacterial agent can be prepared by incorporating antibacterial agent into at least one of the collagen solution to form wound-contacting layer 2, said fibroin film or cross-linked fibrous collagen film to be used as a supporting layer, or said solution containing said substance to afford water permeable film.

BRIEF EXPLANATION OF THE DRAWING

FIG. 1A and FIG. 1B are sectional views showing multi-layer structures of the artificial skin in the present invention; and FIG. 2 is a graph showing the result of tests in which releasing aspect of the antibacterial agent incorporated into the water permeation-controlling layer of the artificial skin in FIG. 1 is examined.

BEST MODE OF THE INVENTION

Now preferred and practical embodiments of the present invention are illustratively shown in the following examples.

A Example of Cell-Penetrable Medical Material and Production Thereof (Example 1 to Example 2)

EXAMPLE 1

One gram of Atelocollagen was dissolved in dilute hydrochloric acid (pH 3.0) to give 0.3% (w/v) solution. This solution was mixed with phosphate buffer with stirring in a thermostart of 4° C. to give collagen solution containing 0.1% (w/v) of ATELOCOLLAGEN, 30 mM disodium phosphate and 100 mM sodium chloride. This solution was left in a thermostart of 37° C. for 1 day to give fibrous ATELOCOLLAGEN solution. This solution was concentrated by centrifuging at 5000 r.p.m. for 10 minutes to give 0.3% (w/v) solution of fibrous ATELOCOLLAGEN. This solution was freezed rapidly at −30° C. and lyophilized to give a sponge. This sponge was dipped in 1% (w/v) solution of hexamethylene diisocyanate in ethanol at room temperature for 24 hours to introduce cross-linking structure. After non-reacted isocyanate was removed by washing with water, the sponge was dipped in distilled water in sterilizing bottle and heated at 121° C. for 30 minutes. Further, it was lyophii lized and heated at 110° C. for 2 hours in vacuum for sterlization to give medical material.

EXAMPLE 2

Preparation was performed in the same manner as in Example 1. Sponge containing cross-linking structure was dipped in distilled water and heated at 90° C. for 30 minutes. After lyophilizing, the sponge was heated at 110° C. under vacuum for 2 hours for sterilization to give medical material.

CONTROL EXAMPLE 1

Preparation was performed in the same manner as in Example 1. Sponge containing cross-linking structure was dipped in distilled water and heated at 40° C. for 30 minutes. After lyophilizing, the sponge was heated t 110° C. under vacuum for 2 hours to give medical material.

CONTROL EXAMPLE 2

Preparation was performed in the same manner as in Example 1. Sponge containing cross-linking structure was heated at 110° C. under vacuum for 2 hours for sterilizing to give medical material.

EXPERIMENT 1

Test of imbedding subcutaneously various medical materials:

Tests of imbedding subcutaneously in rat for observing tissue adaptability on sponges obtained in Example 1–2 and Control Example 1–2 were performed. Sponges in size of 1 cm × 1 cm × 1.5 mm obtained in Example 1–2 and control Example 1–2 were inserted into the opening in about 1.5 cm made by cutting deep on the back of rats, and the wound was closed by stitching with a suture thread. Seventh and 14th days the rats were killed, and dorsal skin tissues were cut off. Cell-penetration into the sponges was observed according to ordinary method of making tissue slices. Table 1 shows the results. As clearly shown in Table 1. Cell-penetration was found to be markedly improved by heating in the presence of water.

TABLE 1

| | Cell-penetration into Sponge | |
|---|---|---|
| Sample | Observation for 7 days | Observation for 14 days |
| Example 1 | Penetration of neutrophil and monocyte into inside of sponges observed | Granulation and cellular infiltration observed |
| Example 2 | Penetration of neutrophil and monocyte into | Granulation and cellular infiltration observed |

TABLE 1-continued

| | Cell-penetration into Sponge | |
|---|---|---|
| Sample | Observation for 7 days | Observation for 14 days |
| | inside of sponges observed | |
| Control Example 1 | Cell-penetration hardly observed/Slight encapsulation present | No penetration into inside of sponges observed/ Surroundings of sponges were encapsulated by strong connective tissues |
| Control Example 2 | Cell-penetration hardly observed/Slight encapsulation present | No penetration into inside of sponges observed/ Surroundings of sponges were encapsulated by strong connective tissues |

EXPERIMENT 2

Decomposition of medical material by enzymes:

Each sponges obtained in Example 1-2 and Control example 1-2 was incubated at 37° C. for 24 hours in 100 unit/ml solution of collagenase derived from bacteria. Amount of hydroxyproline of the collagen eluted into the solution was measured in the lapse of time. Decomposing ratio (%) was calculated by comparing the amount of eluted hydroxyproline with the initial amount of hydroxyproline of the collagen. Table 2 shows the result.

TABLE 2

| | Decomposition of Sponges by Enzymes | |
|---|---|---|
| | Eluted amount of the collagen (%) | |
| Sample | 3rd day | 7th day |
| Example 1 | 2 | 7 |
| Example 2 | 1 | 5 |
| Control Example 1 | 0 | 3 |
| Control Example 2 | 0 | 4 |

It is evident from Table 2 that the medical material of the present invention has almost the same resistance against enzymes as in Control Example.

<B>EXAMPLES OF ARTIFICIAL SKIN AND PRODUCTION THEREOF (EXAMPLE 3-5)

EXAMPLE 3 preparation of Fibroin Matrix:

Purified silk was dissolved in 8M aqueous solution of lithium bromide, and the solution was put in a cellophane tube and dialyzed to water. After confirming that lithium bromide was completely removed, the resultant aqueous solution of fibroin was flowed into a polystyrene vessel, freezed at −10° C. for 24 hours and defreezed at room temperature. After confirming that it became unwoven cloth, it was lyophilized.

EXAMPLE 4

Preparation of Artificial Skin:

1.0% (w/v) solution of fibrous Atelocollagen was prepared in the same manner as in Example 1. This solution was poured into a stainless vat. Further a sponge of fibroin matrix obtained in Example 3 above was gradually put thereon, and the sponge floated on the upper part of the solution. It was rapidly freezed at −30° C. under these conditions, sufficiently freezed and lyophilized at −40° C. under vacuum not exceeding 0.1 Torr. The sponge was dipped in 1% (w/v) solution of hexamethylene diisocyanate in ethanol at room temperature for 24 hours to introduce cross-linking structure. After the non-reacted isocyanate was washed out with water, the sponge was dipped in distilled water in a sterilized bottle, heated at 121° C. for 20 minutes and lyophilized, thereby resulting the sponge in two layers-structure of fibroin matrix and denatured fibrous Atelocollagen matrix. Then 50% solution of silicone adhesive (Silastic type A; Dow Corning) in hexane was applied on a teflon plate with an applicator for making film. Just after application, said sponge was put thereon so that the fibroin matrix would contact with the silicone side, allowed to stand at room temperature for 10 minutes and heated at 60° C. in an oven for at least 1 hour for hardening. Further it was heated at 110° C. under vacuum not exceeding 0.05 Torr, for 2 hours for sterilization to give the desired artificial skin.

EXAMPLE 5

Preparation of Artificial Skin containing Antibacterial Agent:

Preparation was performed in the same manner as in Example 4 except the following. Thus 50% solution of silicone adhesive (Silastic type A: Dow Corning) in hexane containing 50 mg of silver sulfadiazine (AgSD) was applied on a teflon plate with an applicator for making film. The desired artificial skin was prepared by effecting the same procedure as in Example 4 above.

The invention claimed is:

1. Artificial skin which is suitable for application to the site of a wound comprising:
   a wound-contacting layer; and
   a water permeation-controlling area laminated on one side said wound-contacting layer for controlling water permeation;
   said wound-contacting layer being made of denatured collagen obtained by heating cross-linked collagen in the presence of water at a temperature ranging from about 50° to about 125° C. and wherein said denatured collagen lacks antigenicity as the antigenic moiety at the terminus of the collagen molecule has been removed.

2. Artificial skin according to claim 1, in which said wound-contacting layer comprises a sponge form.

3. Artificial skin according to claim 1, in which said denatured collagen has a helix content rate of 0 to 80%.

4. Artificial skin according to claim 1, in which said water permeation-controlling layer is made of non-toxic material selected from the group consisting of silicone resin, polyacrylate ester, polymethacrylate ester and polyurethane.

5. Artificial skin according to claim 1, in which said water permeation-controlling layer has water flux of about 0.1 to 1 mg/cm$^2$/hour.

6. Artificial skin according to claim 2, in which at least one of wound-contacting layer, supporting layer and water permeation-controlling layer contains an antibacterial agent.

7. Artificial skin according to claim 6, in which said antibacterial agent is selected from the group consisting of silver sulfadiazine, gentamycin and silver nitrate.

8. Artificial skin according to claim 1, in which said collagen is fibrous collagen.

9. Artificial skin according to claim 1, in which at least one of said wound-contacting layer and said water permeation-controlling layer contains an antibacterial agent.

10. Artificial skin according to claim 9, in which said antibacterial agent is selected from the group consisting of silver sulfadiazine, gentamicin and silver nitrate.

11. The artificial skin of claim 1, wherein said heating is effected at a temperature ranging from about 90° to about 121° C.

12. Artificial skin which is suitable for application to the site of a wound comprising:
   a supporting layer having a top and bottom side;
   a wound contacting layer laminated to said bottom side of said supporting layer; and
   a water permeation-controlling layer laminated to said top side of said supporting layer,
   said wound-contacting layer comprising denatured collagen obtained by heating cross-linked collagen in the presence of water at a temperature ranging from about 50° to about 125° C. and wherein said denatured collagen lacks antigenicity as the antigenic moiety at the terminus of the collagen molecule has been removed.

13. Artificial skin according to claim 12, in which said wound-contacting layer comprise a sponge form.

14. Artificial skin according to claim 12, in which said denatured collagen has a helix content rate of 0 to 80%.

15. Artificial skin according to claim 12, in which said water permeation-controlling layer is made of non-toxic material selected from the group consisting of silicone resin, polyacrylate ester, polymethacrylate ester and polyurethane 16. Artificial skin according to claim 12, in which said water permeation-controlling layer has a water flux of about 0.1 to 1 mg/cm$^2$/hour.

17. Artificial skin according to claim 12, in which said supporting layer is fibroin.

18. Artificial skin according to claim 12, in which said water permeation controlling layer is about 5 to 200 μm thick.

19. The artificial skin of claim 12, wherein said heating is effected at a temperature ranging from about 90° to about 121° C.

* * * * *

UNITED STATES PATENT AND TRADEMARK OFFICE
CERTIFICATE OF CORRECTION

PATENT NO. : 5,350,583
DATED : September 27, 1994
INVENTOR(S) : Katsutoshi YOSHIZATO et al It is certified that error appears in the above-indentified patent and that said Letters Patent is hereby corrected as shown below:

On the title page in Section [57], kindly delete "(2)".

In Column 1, line 29, delete "enhence" and insert -- enhance --.

In Column 3, line 18, delete "scan" and insert -- can --.

In Column 4, line 10, delete "of".

In Column 4, lines 11-12, delete "Atelocollagen" and insert -- "ATELOCOLLAGEN,"--

In Column 4, line 12, delete "ATELOCOLLAGEN" and insert -- "ATELOCOLLAGEN" --.

In Column 9, line 66, after "of", insert -- collagen having the telopeptide removed, known under the trademark --.

In Column 9, line 66, delete "Atelocollagen" and insert "ATELOCOLLAGEN,"

In Column 10, line 1, delete "thermostart" and insert -- thermostatt --.

In Column 10, line 2, delete "ATELOCOLLAGEN" and insert --"ATELOCOLLAGEN,"--.

In Column 10, line 4, delete "thermostart" and insert -- thermostatt --.

In Column 10, line 5, delete "ATELOCOLLAGEN" and insert "ATELOCOLLAGEN,"-

In Column 10, line 8, delete "ATELOCOLLAGEN" and insert "ATELOCOLLAGEN,"

In Column 10, line 16, delete "lyophii lized" and insert -- lyophilized --.

In Column 12, line 35, between "side" and "said", insert -- of --.

UNITED STATES PATENT AND TRADEMARK OFFICE
CERTIFICATE OF CORRECTION

PATENT NO. : 5,350,583
DATED : September 27, 1994
INVENTOR(S) : Katsutoshi YOSHIZATO et al It is certified that error appears in the above-indentified patent and that said Letters Patent is hereby corrected as shown below:

In Column 14, line 11, delete "a".

Signed and Sealed this

Second Day of May, 1995

Attest:

BRUCE LEHMAN

Attesting Officer

Commissioner of Patents and Trademarks